US007615631B2

(12) United States Patent
Zenoni et al.

(10) Patent No.: US 7,615,631 B2
(45) Date of Patent: Nov. 10, 2009

(54) CRYSTALLINE SOLVATE OF CEFUROXIME ACID

(75) Inventors: Maurizio Zenoni, Paullo (IT); Angelo Giovanni Cattaneo, Monte Marenzo (IT)

(73) Assignee: ACS Dobfar S.p.A., Tribiano (IT)

( * ) Notice: Subject to any disclaimer, the term of this patent is extended or adjusted under 35 U.S.C. 154(b) by 393 days.

(21) Appl. No.: 11/379,132

(22) Filed: Apr. 18, 2006

(65) Prior Publication Data

US 2006/0258636 A1    Nov. 16, 2006

(30) Foreign Application Priority Data

May 13, 2005   (IT)  .......................... MI2005A0871

(51) Int. Cl.
*C07D 501/34*   (2006.01)
(52) U.S. Cl. .................................... 540/222
(58) Field of Classification Search ........................ None
See application file for complete search history.

(56) References Cited

U.S. PATENT DOCUMENTS

| | | | | |
|---|---|---|---|---|
| 3,985,741 | A | * | 10/1976 | Crast et al. .................. 540/230 |
| 4,277,601 | A | | 7/1981 | Thompson et al. |
| 6,833,452 | B2 | * | 12/2004 | Tyagi et al. .................. 540/222 |
| 2004/0092735 | A1 | * | 5/2004 | Deshpande et al. ......... 540/222 |

FOREIGN PATENT DOCUMENTS

| WO | WO 02/20532 A1 | 3/2002 |
|---|---|---|
| WO | WO 2004/041831 A1 | 5/2004 |

OTHER PUBLICATIONS

"Title" The American Heritage® Dictionary of the English Language: Fourth Edition. 2000 <http://www.bartleby.com/61/71/T0237100.html> retrieved from the internet Mar. 20, 2009.*
Title Infoplease.com (Random House Unabridged Dictionary, Copyright © 1997, by Random House, Inc.) <http://dictionary.infoplease.com/title> retrieved from the internet Mar. 20, 2009.*
"Title" Biology-Online.org <http://www.biology-online.org/dictionary/Title> retrieved from the internet Mar. 20, 2009.*

* cited by examiner

*Primary Examiner*—Mark L Berch
(74) *Attorney, Agent, or Firm*—Oblon, Spivak, McClelland, Maier & Neustadt, L.L.P.

(57) ABSTRACT

Crystalline acetonitrile solvate of cefuroxime acid, useful for preparing the antibiotic cefuroxime sodium salt.

4 Claims, 1 Drawing Sheet

CRYSTALLINE SOLVATE OF CEFUROXIME ACID

BACKGROUND OF THE INVENTION

1. Field of the Invention

Cefuroxime is an important antibiotic which has been used for many years in the therapy of gram-negative bacteria infections and is characterised by the formula (I)

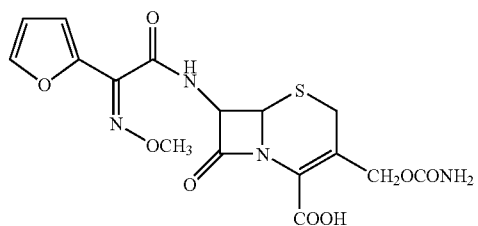

It is administered as the sodium salt by intravenous and intramuscular injection.

The aforesaid formula (I) is clearly derived from the 7-ACA nucleus, which in the chemical synthesis process is subjected to a series of reactions which modify it in positions 3 and 7.

2. Discussion of the Background Art

According to the known art, the aforesaid sodium salt is prepared in injectable sterile form from an intermediate isolated from the aforesaid chemical synthesis process. The intermediate used in the known art is not the cefuroxime acid as would be logical to suppose, because it is very unstable to the extent of becoming visibly coloured after 30 days under vacuum at +5° C. Consequently, so far the background art has not used the non-sterile tetrahydrofuran solvated sodium salt, claimed for example in U.S. Pat. No. 4,277,601 and also cited in U.S. Pat. No. 4,775,750 column 1, line 51. The aforesaid intermediate is put into solution, sterilely filtered and reprecipitated to provide the injectable product.

In industrial practice, it is convenient to produce large batches of intermediate to be stored under suitable conditions, to then be used in small batches for producing the sterile sodium salt. It has however been observed that the stability of the tetrahydrofuran solvated sodium salt is not very high, even though higher than that of the acid as such, in particular because of a moisture content usually $\geq 2\%$ which cannot be reduced in any way. It is therefore apparent that the intermediate cannot be stored at length without observing coloration and degradation which affect the yield and quality of the finished product.

BRIEF SUMMARY OF THE INVENTION

The present inventors have now surprisingly discovered that both a solvated cefuroxime useful for preparing the antibiotic cefuroxime sodium salt and a practically anhydrous crystalline solvate of cefuroxime acid can be prepared by treatment with acetonitrile. This solvate has demonstrated a stability considerably higher than that of the tetrahydrofuran solvated sodium salt.

In this manner the aforesaid problems of stability and coloration of the intermediate are overcome, with evident advantages in terms of final yield and quality. In addition to the aforesaid advantages, it has also been noted that isolation of the acetonitrile acid crystalline solvate results in a yield higher than that obtainable if isolating the cefuroxime acid as such: in this respect, for equal synthesis the yield of cefuroxime acid, in terms of activity in the crystalline solvate, is at least 5% higher than the activity of cefuroxime acid isolated as such. In either case, the cefuroxime acid as such or its acetonitrile crystalline solvate is put into solution, sterilely filtered and reprecipitated as sodium salts by known methods, in a manner similar to that for tetrahydrofuran solvated sodium salt.

DETAILED DESCRIPTION OF THE INVENTION

EXAMPLE 1

Figure 1:
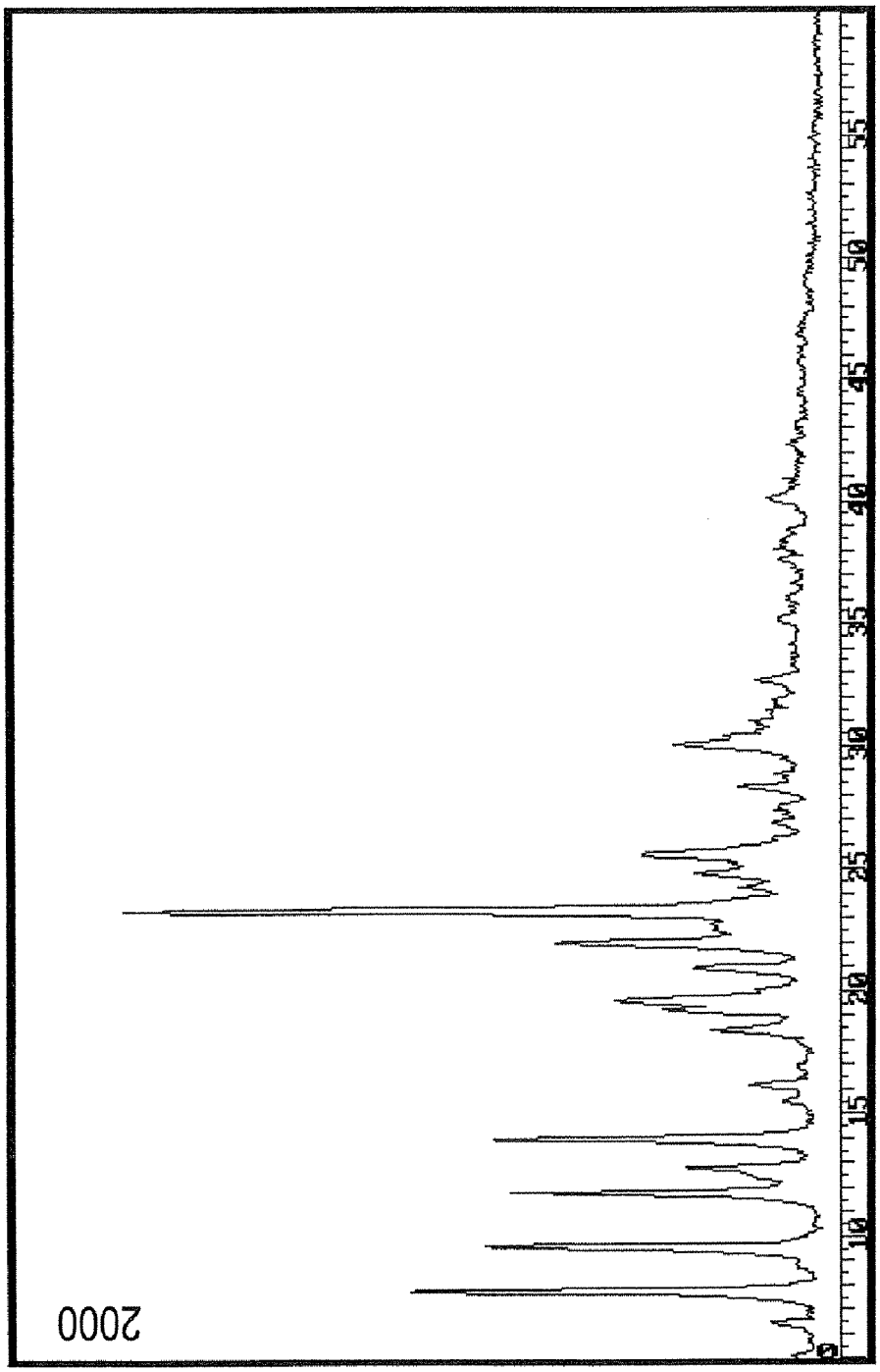
FIG. 1 is a diffraction spectrum for the crystalline solvate of cefuroxime acid acetonitrile solvate.

A solution of cefuroxime acid in a mixture of ethyl acetate and methylene chloride is prepared from 278 g of 7-ACA in known manner. The solution is concentrated under vacuum to 1100 ml, cooled to +15° C. and diluted with 1000 ml of acetonitrile. After this addition the solution is further concentrated under vacuum and then diluted with a further 1000 ml of acetonitrile.

The mixture is cooled to +5° C. for 90 min under slow agitation with resultant precipitation of the acetonitrile solvate of cefuroxime acid. The precipitate is filtered off and washed with acetonitrile to obtain 430 g of wet product. By drying at 55° C. under vacuum, 350 g of dry solvate are obtained having K.F. 0.2%, concentration on dry basis 84.0%, acetonitrile 13.8%.

The product is stored at ambient temperature without any loss of strength or colour variation, even after six months.

The diffraction spectrum for the sample product was determined by a ROGAKU DMAX II diffractometer operating with Cu—Kα ($\lambda$=1.5405 A°) 40 kV and 40 mA, graphite monochromator on reflected beam, scanning by 0.02 degrees per step and 1 second for each step.

The spectrum is shown in the accompanying FIG. 1, while the numerical data are given in the following table:

| Anticathode: Cu Kα<br>Voltage: 40 kV<br>Angle (2-Theta) | Filter: Ni<br>Current: 40 mA<br>Relative intensity |
|---|---|
| 6.43 | 9.52 |
| 7.78 | 59.46 |
| 8.90 | 5.94 |
| 9.54 | 49.19 |
| 11.78 | 45.73 |
| 12.79 | 21.51 |
| 13.96 | 48.33 |
| 15.48 | 7.61 |
| 16.17 | 12.23 |
| 17.84 | 5.82 |
| 18.39 | 17.88 |
| 18.68 | 7.61 |
| 19.24 | 24.68 |
| 19.57 | 31.31 |
| 20.87 | 20.07 |
| 21.94 | 39.56 |
| 22.50 | 17.30 |
| 22.73 | 17.82 |
| 22.83 | 16.38 |
| 23.26 | 100.00 |
| 24.22 | 13.78 |
| 24.78 | 20.01 |
| 25.12 | 15.34 |
| 25.61 | 27.28 |

-continued

| Anticathode: Cu Kα Voltage: 40 kV Angle (2-Theta) | Filter: Ni Current: 40 mA Relative intensity |
|---|---|
| 26.17 | 9.05 |
| 26.84 | 9.11 |
| 26.80 | 8.65 |
| 27.34 | 8.82 |
| 27.50 | 8.36 |
| 28.23 | 13.90 |
| 28.64 | 7.67 |
| 28.79 | 8.65 |
| 28.99 | 6.40 |
| 29.34 | 7.79 |
| 29.97 | 23.07 |
| 30.94 | 12.23 |
| 31.83 | 8.94 |
| 32.20 | 6.98 |
| 32.62 | 11.53 |
| 33.28 | 6.46 |
| 33.94 | 6.11 |
| 33.95 | 6.52 |
| 34.08 | 6.34 |
| 34.36 | 6.00 |
| 35.09 | 8.25 |
| 35.64 | 6.57 |
| 37.53 | 7.61 |
| 38.13 | 7.96 |
| 38.30 | 8.07 |
| 38.45 | 7.04 |
| 38.76 | 7.09 |
| 39.61 | 5.82 |
| 40.07 | 9.98 |
| 40.47 | 6.75 |
| 40.64 | 6.06 |
| 40.78 | 7.44 |
| 41.00 | 5.94 |
| 41.19 | 6.11 |
| 42.23 | 7.21 |
| 46.73 | 5.82 |

What is claimed is:

1. A crystalline solvate of cefuroxime acid of formula

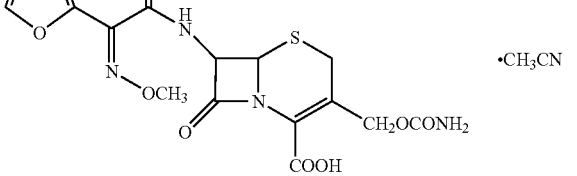

(II)

comprising from 10 to 16% of acetonitrile, K.F. 0.2%, and greater than or equal to 80.0% of the cefuroxime acid calculated on dry basis.

2. A crystalline solvate of cefuroxime acid of formula

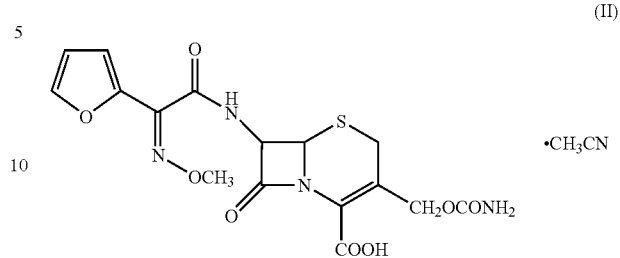

(II)

comprising from 10 to 16% of acetonitrile.

3. The crystalline solvate of cefuroxime acid of claim 1, wherein the crystalline solvate of cefuroxime acid has a crystalline structure with an Xr diffraction spectrum with the following characteristics:

| Anticathode: Cu Kα Voltage: 40 kV Angle (2-Theta) | Filter: Ni Current: 40 mA Relative intensity |
|---|---|
| 6.43 | 9.52 |
| 7.78 | 59.46 |
| 8.90 | 5.94 |
| 9.54 | 49.19 |
| 11.78 | 45.73 |
| 12.79 | 21.51 |
| 13.96 | 48.33 |
| 15.48 | 7.61 |
| 16.17 | 12.23 |
| 17.84 | 5.82 |
| 18.39 | 17.88 |
| 18.68 | 7.61 |
| 19.24 | 24.68 |
| 19.57 | 31.31 |
| 20.87 | 20.07 |
| 21.94 | 39.56 |
| 22.50 | 17.30 |
| 22.73 | 17.82 |
| 22.83 | 16.38 |
| 23.26 | 100.00 |
| 24.22 | 13.78 |
| 24.78 | 20.01 |
| 25.12 | 15.34 |
| 25.61 | 27.28 |
| 26.17 | 9.05 |
| 26.84 | 9.11 |
| 26.80 | 8.65 |
| 27.34 | 8.82 |
| 27.50 | 8.36 |
| 28.23 | 13.90 |
| 28.64 | 7.67 |
| 28.79 | 8.65 |
| 28.99 | 6.40 |
| 29.34 | 7.79 |
| 29.97 | 23.07 |
| 30.94 | 12.23 |
| 31.83 | 8.94 |
| 32.20 | 6.98 |
| 32.62 | 11.53 |
| 33.28 | 6.46 |
| 33.94 | 6.11 |
| 33.95 | 6.52 |
| 34.08 | 6.34 |
| 34.36 | 6.00 |
| 35.09 | 8.25 |
| 35.64 | 6.57 |
| 37.53 | 7.61 |
| 38.13 | 7.96 |
| 38.30 | 8.07 |

| Anticathode: Cu Kα<br>Voltage: 40 kV<br>Angle (2-Theta) | Filter: Ni<br>Current: 40 mA<br>Relative intensity |
|---|---|
| 38.45 | 7.04 |
| 38.76 | 7.09 |
| 39.61 | 5.82 |
| 40.07 | 9.98 |
| 40.47 | 6.75 |
| 40.64 | 6.06 |
| 40.78 | 7.44 |
| 41.00 | 5.94 |
| 41.19 | 6.11 |
| 42.23 | 7.21 |
| 46.73 | 5.82. |

4. The crystalline solvate of cefuroxime acid of claim 2, wherein the crystalline solvate of cefuroxime acid has a crystalline structure with an Xr diffraction spectrum with the following characteristics:

| Anticathode: Cu Kα<br>Voltage: 40 kV<br>Angle (2-Theta) | Filter: Ni<br>Current: 40 mA<br>Relative intensity |
|---|---|
| 6.43 | 9.52 |
| 7.78 | 59.46 |
| 8.90 | 5.94 |
| 9.54 | 49.19 |
| 11.78 | 45.73 |
| 12.79 | 21.51 |
| 13.96 | 48.33 |
| 15.48 | 7.61 |
| 16.17 | 12.23 |
| 17.84 | 5.82 |
| 18.39 | 17.88 |
| 18.68 | 7.61 |
| 19.24 | 24.68 |
| 19.57 | 31.31 |
| 20.87 | 20.07 |
| 21.94 | 39.56 |
| 22.50 | 17.30 |
| 22.73 | 17.82 |
| 22.83 | 16.38 |
| 23.26 | 100.00 |
| 24.22 | 13.78 |
| 24.78 | 20.01 |
| 25.12 | 15.34 |
| 25.61 | 27.28 |
| 26.17 | 9.05 |
| 26.84 | 9.11 |
| 26.80 | 8.65 |
| 27.34 | 8.82 |
| 27.50 | 8.36 |
| 28.23 | 13.90 |
| 28.64 | 7.67 |
| 28.79 | 8.65 |
| 28.99 | 6.40 |
| 29.34 | 7.79 |
| 29.97 | 23.07 |
| 30.94 | 12.23 |
| 31.83 | 8.94 |
| 32.20 | 6.98 |
| 32.62 | 11.53 |
| 33.28 | 6.46 |
| 33.94 | 6.11 |
| 33.95 | 6.52 |
| 34.08 | 6.34 |
| 34.36 | 6.00 |
| 35.09 | 8.25 |
| 35.64 | 6.57 |
| 37.53 | 7.61 |
| 38.13 | 7.96 |
| 38.30 | 8.07 |
| 38.45 | 7.04 |
| 38.76 | 7.09 |
| 39.61 | 5.82 |
| 40.07 | 9.98 |
| 40.47 | 6.75 |
| 40.64 | 6.06 |
| 40.78 | 7.44 |
| 41.00 | 5.94 |
| 41.19 | 6.11 |
| 42.23 | 7.21 |
| 46.73 | 5.82. |

\* \* \* \* \*